United States Patent [19]

Aron-Samuel et al.

[11] 3,935,313

[45] Jan. 27, 1976

[54] PHARMACEUTICAL COMPOSITION CONTAINING N-(3-DIETHYL-AMINOPROPYL)-4-NITRO-1-OXIDE-PYRIDINE-2-CARBOXAMIDE AND PROCESS FOR THE TREATMENT OF HYPERTENSION THEREWITH

[75] Inventors: Jan Marcel Didier Aron-Samuel, Suresnes; Jean Jacques Sterne, Argenteuil, both of France

[73] Assignee: Jan Marcel Didier Aron-Samuel, Suresnes, France

[22] Filed: May 29, 1974

[21] Appl. No.: 474,316

Related U.S. Application Data

[63] Continuation-in-part of Ser. No. 233,718, March 10, 1972, abandoned.

[30] Foreign Application Priority Data

Mar. 29, 1971 United Kingdom................ 8084/71

[52] U.S. Cl................................ 424/266; 424/263
[51] Int. Cl.² ................. A61K 31/455; A61K 31/44
[58] Field of Search........................... 424/263, 266

[56] References Cited
OTHER PUBLICATIONS

Profft, et al., Chem. Abstracts, Vol. 56, No. 9, 10090-h to 10091-i, Apr. 30, 1962.

*Primary Examiner*—Stanley J. Friedman
*Assistant Examiner*—Daren M. Stephens
*Attorney, Agent, or Firm*—Young & Thompson

[57] ABSTRACT

This invention relates to a process for the treatment of hypertension and of the disorders derived therefrom, comprising administering to a patient suffering from hypertension a therapeutically effective amount of a compound selected from N-(3-diethyl-aminopropyl)-4-nitro-1-oxide-pyridine-2-carboxamide and its acid addition salts with therapeutically acceptable acids.

11 Claims, No Drawings

PHARMACEUTICAL COMPOSITION CONTAINING N-(3-DIETHYL-AMINOPROPYL)-4-NITRO-1-OXIDE-PYRIDINE-2-CARBOXAMIDE AND PROCESS FOR THE TREATMENT OF HYPERTENSION THEREWITH

The present application is a continuation-in-part of application Ser. No. 233,718 filed March 10, 1972 and now abandoned.

This application concerns a process for the treatment of hypertension and the disorders derived therefrom. It relates also to pharmaceutical compositions having an antihypertensive activity.

This invention provides a process for the treatment of hypertension and the disorders derived therefrom, comprising administering to a patient suffering from hypertension a therapeutically effective amount of a compound selected from N-(3-diethylaminopropyl)-4-nitro-1-oxide-pyridine-2-carboxamide and its acid addition salts with pharmaceutically acceptable acids.

This invention provides also a pharmaceutical composition having an anti-hypertensive activity, containing a therapeutically effective amount of a compound selected from N-(3-diethylaminopropyl)-4-nitro-1-oxide-pyridine-2-carboxamide and its acid addition salts with pharmaceutically acceptable acids.

Typical examples of pharmaceutically acceptable salts are the acid addition salts with hydrochloric, sulfuric, phosphoric, methane sulfonic, maleic, succinic, pamoic, acetic, fumaric, lactic, aspartic and citric acids.

The materials used according to the present invention may be administered by the oral, parenteral or rectal route. The products may be protected -or not- by a pharmaceutically acceptable coating. They may be administered optionally in combination with pharmaceutical excipients such as the usual excipients described in USP XIII and in the Pharmaceutical Codex.

The products may be administered typically in the form of tablets, capsules, suppositories, drinkable solutions and injectable solutions. The daily dosage regimen may be from 30 mg to 5000 mg and preferably from 200 to 3000 mg. When formulated in unit dosage form, each unit dose may contain from 10 mg to 1000 mg active ingredient. The products used according to this invention may be prepared according to the following reaction sheme:

ther two hours after completion of the addition. Isopropyl alcohol (50 cc) saturated with dry hydrochloric acid is then added. The resulting solid is washed with 2 × 50 cc acetone. The product is then suction filtered, dried and recrystallised from 95% ethyl alcohol (300 cc). After drying, there are obtained 53.5 g of N-(3-dimethylaminopropyl)-4-nitro-1-oxide-pyridine-2-carboxamide hydrochloride (LA 2511). Yield 80.3%.

Melting point (capillary tube): 180°C, with introduction at 169°C and heating at a rate of 2°C per minute.

Analysis: Theoretical, %: C, 46.92; H, 6.36; N, 16.83; Cl, 10.66. Found %: C, 46.77; H, 6.42; N, 16.91; Cl, 10.77.

The following salts are prepared according to the same procedure:

Fumarate: M.P. = 161°C.
Methane sulfonate: M.P. = 107°–109°C.

Results of pharmacological tests demonstrating the low toxicity and the anti-hypertensive effectiveness of the products of this invention are given below. The compound used for such tests is the hydrochloride (LA 2511).

Acute toxicity

Acute toxicity is 2000 mg/kg as evaluated according to the method of Lichtfield and Wilcoxon (J. Pharm. Exp. Ther., 1949, 96, 99–113).

Chronic toxicity

On chronic treatment administration during 6 months to Rhesus monkeys and rats, the compound produced no toxic effect even at the maximum dose tested (400 mg/kg). No teratogenic effect was apparent either in rats at the 600 mg/kg test dosage or in rabbits at a dosage of 200 mg/kg.

Anti-hypertensive effect

The anti-hypertensive effect was investigated:
1. in dogs made hypertensive by the bilateral destruction of the sensory endings of the sino-carotid area;
2. in rats made hypertensive by implantation of two 25 mg deoxycorticosterone pellets combined with a sodium enriched diet;
3. in rats made hypertensive according to Goldblatt's method (unilateral renal arterial constriction with contralateral nephrectomy).

In all three types of experimental hypertension, relating to models usually highly resistant to therapy, the compound was found to possess substantial consistent efficiency.

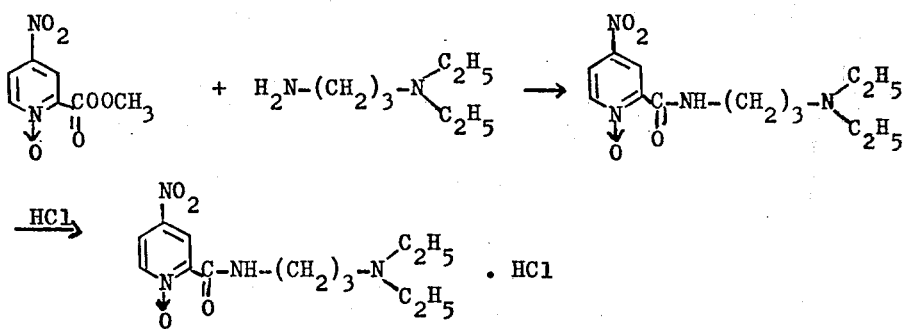

The following operating procedure is used: 200 cc isopropyl alcohol and 39.6 g of 4-nitro-1-oxide-pyridine-2-carboxylic acid methyl ester are introduced into a reactor. Diethylaminopropylamine (26 g) is added to the resulting suspension. Stirring is maintained a fur- This efficiency is extended, when the compound is administered in combination with diuretics.

The pharmacological properties evidenced by this compound have led to its use as an anti-hypertensive material in Man.

The compound was found to be free from toxicity and to have an excellent efficiency. The effect on the diastolic pressure, particularly, is well established.

I. Effects in normotensive subjects

Prior to the therapeutic tests, toxicological and clinical pharmacological investigations were conducted in normotensive Man. Said investigations have shown that, under such conditions, when administered orally at a daily dosage regimen within a range from 200 mg to 5 g, the compound produced a moderate gradual depression of the blood pressure. The systolic pressure is depressed by 2 to 4 cm of mercury, while the diastolic pressure is depressed by 2 cm, on the average. A more substantial depression is noted under orthostatic conditions. No deleterious influence was found to affect the heart. No modifications were ever noted in the electrocardiogram and in numerous biological tests, particularly in tests relating to the blood count and picture, sedimentation rate, phosphatases, transaminases, azotemia, glycemia, albuminuria, urinary sediment, creatinemia, creatinuria, creatinine clearance, blood and urinary ion concentration, blood proteins, cholesterolemia and blood lipids.

Specific examples are reported:

VUI... Robert

Dosage of compound administered: 1 tablet containing 400 mg active ingredient during 1 week, 2 tablets during 1 week, 3 tablets during 3 weeks.

Initial blood pressure; recumbent position: morning: 15/8, evening: 13.5/7.

After 5 weeks of treatment: morning: 10.5/7; evening: 10.6.

Excellent tolerance.

CHA... Paul

Dosage of compound administered: 1 tablets containing 400 mg active ingredient during 3 weeks, 2 tablets during the 5 following weeks.

Initial blood pressure: recumbent position: morning: 14/8; evening: 13/8.

Blood pressure after treatment: recumbent position: morning: 12/6, evening: 11/6.

Excellent tolerance.

II. Therapeutic effects of the compound in hypertensive subjects

About a hundred patients were treated with the compound during several months. The results obtained were compared with those usually observed with other reference anti-hypertensive treatments.

1. Diuretics and particularly - thiazidics such as chlorothiazide, hydrochlorothiazide,
   - iso-indoline derivatives: chlorthalidone, clorexolone,
   - halogenophenylsulfamides: clopamide,
   - thiachromane derivatives: meticrane.
2. Na reabsorption inhibitors: furosemide, etacrynic acid.
3. Aldosterone antagonists, particularly:
   a. specific competitors: spironolactone, canrenone,
   b. non-specific antagonists: triamterene, amiloride.
4. α-Methyldopa.
5. Guanethidines, particularly: guanethidine, betanidine, guanoxan sulfate and bretylium.
6. Hydralazines, particularly: hydralazine, dihydralazine and hydrocarbazine.
7. Reserpinics such as reserpine, methoserpidine, reserpiline, syrosyngopine.
8. Central hypotensive drugs such as clonidine.
9. Hypotensive combinations of a diuretic and another type of hypotensive material, particularly:

Reserpine: 0.1 mg, bendroflumethiazide: 0.1 mg,
Methoserpidine: 20 mg, cyclothiazide: 4 mg, diprophylline: 50 mg
Rescinnamine: 0.5 mg, paraflutizide: 2.5 mg, meprobamate: 200 mg, folsentol: 20 mg.

II-1 Treatment using the compound alone

The compound was tested alone at dosages from 300 mg to 5 g daily. In more than half the hypertensive subjects, it produced a substantial depression of the blood pressure, in excess of 4 cm of mercury with respect to the systolic pressure and in excess of 2 cm of mercury with respect to the diastolic pressure. One-fourth of the patients exhibited a moderate depression, of about 2 cm with respect to the systolic pressure and about 1 cm with respect to the diastolic pressure. The depression is not sudden, but it occurs at an early stage, within a few hours or a few days. Less than one-fourth of the subjects were non-influenced. The results just set forth relate to determinations made with the patients in a recumbent position. When the blood pressure is taken with the subjects in a standing position, the values obtained are more highly depressed, becoming close to normal or even attaining the normal value in cases where no depression was apparent with the subjects in a recumbent position. None of the subjects exhibited troublesome orthostatic hypotension induced fits of faintness. The following general example is given:

Clinical experimentation involving 22 hospital patients.

Procedure: The patients selected suffer from true hypertension involving both systolic pressure and diastolic pressure. Before starting treatment with the compound, it was ascertained, during a period of time of 8 days, in the absence of any hypotensive treatment, that this hypertension was stable in the morning, at noon and in the evening, in standing, sitting and recumbent positions.

Evaluation criteria:

1. Effect on blood pressure: the result was evaluated on the basis of the blood pressure depression, expressed as cm of mercury, according to the following criteria:

| Result | Nil | Fair | Good | Very good |
| --- | --- | --- | --- | --- |
| Systolic pressure depression | 0 | < 3 cm | 3–4 cm | > 4 cm |
| Diastolic pressure depression | 0 | <1.5 cm | 1.5–2 cm | >2 cm |

2. Effect on functional signs: headaches, dizziness, floating specks, ear buzzing.

Under such conditions, the following results were obtained:
13 "good" and "very good" results,
5 "fair" results
4 "nil" results.

The following specific examples are given:

PER... Robert.

Essential hypertension with functional signs (headaches, earbuzzing.

Dosage of compound administered: 7 days at 2, then 4, then 6 tablets per day (each tablet containing 400 mg active compound), and then 21 days at 6 tablets per day.

Blood pressure prior to treatment: recumbent: 21½/12; sitting: 21/12; standing: 20½/12.

Blood pressure after treatment: recumbent: 15/10; sitting: 16½/10; standing: 17/10.

Disappearance of the functional signs. Excellent tolerance.

BLA... Isaac.

Arterial hypertension - atheroma.

Dosage of compound administered: 6 tablets containing 400 mg active compound daily during 15 days, followed by 4 tablets daily during 15 days.

Blood pressure prior to treatment: recumbent: 20/13; sitting: 20/12½; standing: 19½/10.

Blood pressure after treatment: recumbent: 19/1; sitting: 19/10; standing: 14½/10.

Very good systemic tolerance. Bitter taste on intake of the tablet.

When administration of the pharmaceutical composition is interrupted, the blood pressure returns to its former levels within 3–4 days to decrease again upon a second administration of the compound.

The only side-effect noted was the occurrence of a few cases of gastric pains and nausea which disappear when the pharmaceutical composition is ingested in the middle of a meal and/or when the dosages are decreased.

The effects on blood pressure were generally much more rapid and much more positive than with diuretic drugs, α-methyldopa and other hypotensive agents, particularly with respect to the diastolic pressure, the physiological significance of which known.

II - 2 Treatment with the compound used in combination with other anti-hypertensive materials Combinations of the compound of this invention with other anti-hypertensive agents were also investigated.

The most important combination is that with diuretic drugs, as predicted from the efficiency data provided by the pharmacological investigation. A reduction of the dosage of compound of about 50% and/or a threefold duration of the action are obtained.

The compound may also safely be combined with other anti-hypertensive materials currently used, such as those mentioned hereinabove.

The following specific examples are given:

SUF... Auguste

Old arterial hypertension - atheroma.

Functional signs (floating specks, headaches, earbuzzing).

Dosage of compound administered: 5 tablets containing 400 mg active compound daily during 30 days. Associated treatment: salt-free diet, potassium chloride, furosemide: one 40 mg tablet, 3 times a week.

Blood pressure prior to treatment: recumbent: 24/13; sitting: 24/12; standing: 24/12.

Blood pressure after treatment: recumbent: 18/10; sitting: 18/10; standing: 17/9. Marked decrease of the functional signs. Very good digestive and systemic tolerance.

GAU... Albert

Arterial hypertension. Atheroma. Obesity. Heavy smoker.

Functional signs (floating specks, headaches, dizziness, earbuzzing).

Dosage of compound administered: 5 tablets containing 400 mg active material, daily during 30 days. Associated treatment: potassium chloride, altizide: 15 mg; spironolactone: 25 mg.

Blood pressure prior to treatment: recumbent: 21/13; sitting: 21/13; standing: 20/12½.

Blood pressure after treatment: recumbent: 16/10; sitting: 16/10; standing: 14/9.

Improvement of the functional signs. Very good systemic tolerance. Fair digestive tolerance.

TRU... Yves

Arterial hypertension which had been known to exist for a number of years. Irregularly treated with various reserpinic drugs.

Strong functional signs (headaches, dizziness). Treated during one month with α-methyldopa: 2, then 4, then 6 tablets per day, containing each 250 mg active ingredient.

Blood pressure prior to treatment with α-methyldopa: recumbent: 23/12; sitting: 23/11½; standing: 22/12.

Blood pressure after treatment with α-methyldopa: recumbent: 21/11½; sitting: 21/11½; standing 20/11. Slight decrease of the functional signs.

Treatment during one month with the compound of this invention: 4 tablets daily, containing each 400 mg active ingredient, taken two at a time, plus 4 tablets daily of α-methyl dopa, containing each 250 mg active ingredient, taken two at a time.

Blood pressure after treatment: recumbent: 19/10½; sitting: 19/10; standing: 18/9.

Marked decrease of the functional signs, particularly of the headaches.

Thus, on oral administration of daily dosages from 200 mg to 5 g, the compound of this invention was found to be an anti-hypertensive agent free from toxicity, well tolerated, having a rapid but gradual action.

It may be combined with other drugs of the same faimly and particularly with diuretics, with which it constitutes a particularly efficient combination.

Examples of pharmaceutical compositions are given below:

Tablets containing each 600 mg active substance

| Substance (hydrochloride) (LA 2511) | 600 mg |
|---|---|
| Maize starch (AMIJEL) | 100 mg |
| Magnesium stearate | 7 mg |
| Micronized talc | 28 mg |
| Deionized water | Q.S. |

Tablets containing each 400 mg active substannce

| Substance (hydrochloride) | 400 mg |
|---|---|
| Lactose | 100 mg |
| Icing sugar | 50 mg |
| Ethyl alcohol (40%) | Q.S. |
| Maize starch | 10 mg |
| Magnesium stearate | 7 mg |

Tablets containing each 600 mg active substance
-continued

Capsules

| | | |
|---|---|---|
| | Substance (hydrochloride) | 300 mg |
| | Magnesium stearate | 3 mg |

Injectable ampullae

| | | |
|---|---|---|
| | Substance (hydrochloride) | 250 mg |
| | NaCl | 16,2 mg |
| | Injectable water to make | 5 ml |

Syrup

| | | |
|---|---|---|
| Substance (hydrochloride) | | 3 g |
| Preservatives | p-hydroxybenzoate methyl ester | 80 mg |
| | p-hydroxybenzoate propyl ester | 40 mg |

Flavored sugar solution to make 100 ml each tablespoonful containing 600 mg of substance.

Having now described our invention what we claim as new and desire to seam by letters Patent is:

1. Process for the treatment of hypertension, comprising administering to a patient suffering from hypertension a therapeutically effective amount of a compound selected from the group consisting of N-(3-diethylaminopropyl)-4-nitro-1-oxide-pyridine-2-carboxamide and its acid addition salt with a pharmaceutically acceptable acid.

2. The process for the treatment of hypertension, as claimed in claim 1, comprising administering daily to said patient from 30 mg to 5000 mg of a compound selected from the group consisting of N-(3-diethylaminopropyl)-4-nitro-1-oxide-pyridine-2-carboxamide and its acid addition salt with a pharmaceutically acceptable acid.

3. Process for the treatment of hypertension, as claimed in claim 2, comprising administering daily to said patient from 200 mg to 3000 mg of a compound selected from the group consisting of N-(3-diethylamino-propyl)-4-nitro-1-oxide-pyridine-2-carboxamide and its acid addition salt with a pharmaceutically acceptable acid.

4. Pharmaceutical composition having an anti-hypertensive activity comprising a therapeutically effective amount of a compound selected from the group consisting of N-(3-diethylamino-propyl)-4-nitro-1-oxide-pyridine-2-carboxamide and its acid addition salt with a pharmaceutically acceptable acid together with a pharmaceutical carrier.

5. Pharmaceutical composition as claimed in claim 4, in unit dosage form, each unit dose containing 10 mg to 1000 mg of a compound selected from the group consisting of N-(3-diethylaminopropyl)-4-nitro-1-oxide-pyridine-2-carboxamide and its acid addition salt with a pharmaceutically acceptable acid together with a pharmaceutical carrier.

6. Pharmaceutical composition as claimed in claim 4, in a form suitable for oral administration.

7. Pharmaceutical composition as claimed in claim 6, in the form of a tablet.

8. Pharmaceutical composition as claimed in claim 6, in the form of a capsule.

9. Pharmaceutical composition as claimed in claim 6, in the form of a syrup.

10. Pharmaceutical composition as claimed in claim 4, in a form suitable for parenteral administration.

11. Pharmaceutical composition as claimed in claim 10, in the form of an injectable solution.

* * * * *